(12) United States Patent
Kanie (10) Patent No.: US 7,931,912 B2
(45) Date of Patent: Apr. 26, 2011

(54) ENTERAL NUTRITION PRODUCT AND METHOD FOR PREPARING THE SAME

(76) Inventor: Jiro Kanie, Nagoya (JP)

( * ) Notice: Subject to any disclaimer, the term of this patent is extended or adjusted under 35 U.S.C. 154(b) by 550 days.

(21) Appl. No.: 10/826,165

(22) Filed: Apr. 16, 2004

(65) Prior Publication Data

US 2004/0197381 A1 Oct. 7, 2004

Related U.S. Application Data

(63) Continuation of application No. PCT/JP02/10704, filed on Oct. 15, 2002.

(30) Foreign Application Priority Data

Oct. 22, 2001 (JP) .................................. 2001-323124
Apr. 10, 2002 (JP) .................................. 2002-108094

(51) Int. Cl.
*A61K 47/00* (2006.01)
*A23L 1/30* (2006.01)

(52) U.S. Cl. .............................. 424/439; 426/72; 426/73

(58) Field of Classification Search .................. 424/490, 424/73, 400–401, 439; 426/662, 74–76; 428/74–76, 662
See application file for complete search history.

(56) References Cited

U.S. PATENT DOCUMENTS

| | | | | |
|---|---|---|---|---|
| 5,232,733 A | * | 8/1993 | Resmer | 426/590 |
| 5,543,169 A | * | 8/1996 | Colarow et al. | 426/662 |
| 5,716,639 A | * | 2/1998 | Carlsson et al. | 424/450 |
| 5,985,339 A | * | 11/1999 | Kamarei | 426/72 |
| 6,187,334 B1 | | 2/2001 | Yamagata et al. | |

FOREIGN PATENT DOCUMENTS

| | | |
|---|---|---|
| JP | 7-147932 A1 | 6/1995 |
| JP | 08-196236 A1 | 8/1996 |
| JP | 10-155432 A1 | 6/1998 |
| JP | 11-009222 A1 | 1/1999 |
| JP | 2000-152975 A1 | 6/2000 |
| JP | 2000-169397 A1 | 6/2000 |
| JP | 2000-217544 A1 | 8/2000 |
| JP | 2000-279107 A1 | 10/2000 |
| JP | 2001-000144 A1 | 1/2001 |
| JP | 2001-504339 A1 | 4/2001 |
| WO | WO 00/13529 A1 | 3/2000 |

OTHER PUBLICATIONS

Ying et al, Molded Rice Pudding with Chestnuts recipe, 1986, The New Good HouseKeeping Cookbook, p. 542.*
Kabushiki et al, Total Parenterl Nutriion and Enteral Nutrition, May 31, 2001, Nippon Rinsho, vol. 59, No. 782, Suppl. 5, p. 283 and 307.*
Ying, MOlded Rice Pudding with Chestnuts, recipe entry; The Good Houskeeping Cookbook, 1986, p. 542.*
Kabushiki et al, total Parenteral Nutritional and Enteral Nutrition, p. 283-307, Suppl. 5, Nippon Rinsho, vol. 59, No. 782.*
Molded Rice pusing with chesnuts recipe entry; The New God housekeeing Cookbook, 1986, p. 542.*
Kabushuiki et al (Total Parenteral Nutritional and Enteral Nutrition, p. 283-307, Suppl 5, Nippon Rinsho, vol. 59, No. 782).*
Molded Rice Pudding with chesnuts recipe entry; The New good Housekeeping Cookbook, 1998, p. 542.*
Kabushuiki et al (Total Parenteral Nutritional and Enteral Nutrition); p. 283-307, Suppl 5, Nippon Rinsho, vol. 59, No. 782.*
Ying et al, Rice Pudding, 1986, The New Good Housekeeping Cookbook, p. 542.*
Ying et al, Quick Chocolate-Almond Mousse, 1986, The New Goog Housekeeping Cookbook, p. 530.*
Kabushiki et al, Total Parenteral Nutritional and Enteral Nutrition, Nippon, Rlnsho, col. 59, No. 782, pp. 283-307.*
Kabushiki, et al, Total Parenteral Nutritional and Enteral Nutrition, Nippon, Rishino, col. 59, No. 782, pp. 283-307.*
http://www.geocities.com/Tokyo/Courtyard/8761/f07e.htm.*
"Total Parenteral Nutrition and Enteral Nutrition," Nippon Rinsho vol. 59, No. 782, Suppl. 5, published May 31, 2001 by Kabushiki Kaisha Nippon Rinsho Sha, pp. 283 and 307.

* cited by examiner

*Primary Examiner* — Michael G Hartley
*Assistant Examiner* — Micah-Paul Young
(74) *Attorney, Agent, or Firm* — Burr & Brown (57) ABSTRACT

An enteral nutrition product is provided for enteral administration directly to the stomach or intestines of a patient from an external container upon the application of pressure to the external container. The enteral nutrition product is a semi-solid material having a substantially self-supporting consistency that deforms under an externally applied load without liquefying and that is capable of containing a higher concentration of a nutrient component than a fluid. The semi-solid material includes a mixture of a nutrient solution and a semi-solidifying agent that is one of agar and a whole egg. The self-supporting consistency of the semi-solid enteral nutrition product remains substantially unchanged before, during, and after being enterally administered into the patient, and is further maintained within the stomach or the intestines of the patient such that the enteral nutrition product does not liquefy due to the body temperature of the patient.

6 Claims, 7 Drawing Sheets

| ID | AGE | SEX | UNDERLYING DISEASE | GASTRO-ESOPHAGEAL REFLUX | | REGION OF REFLUX | | DISTANCE FROM CARDIA | |
|---|---|---|---|---|---|---|---|---|---|
| | | | | LIQUID | SEMI-SOLID | LIQUID | SEMI-SOLID | LIQUID | SEMI-SOLID |
| 58 | 82 | F | DEMENTIA | − | − | | | | |
| 245 | 81 | F | DEMENTIA | − | − | | | | |
| 261 | 90 | F | DEMENTIA | + | − | 7 | | 13 | 13 |
| 395 | 53 | F | SEQUELA OF CEREBRAL INFRACTION | − | − | | | | |
| 467 | 87 | F | DEMENTIA | + | + | 4 | 6 | 13 | |
| 559 | 80 | F | DEMENTIA | + | − | 9 | | 9 | 10 |
| 560 | 82 | M | DEMENTIA | + | + | 4 | 4 | 13 | 13 |
| 571 | 87 | F | SEQUELA OF CEREBRAL INFRACTION | + | − | 1 | | 4 | |
| 576 | 84 | M | SEQUELA OF CEREBRAL INFRACTION | + | − | 12 | | 15 | |
| 582 | 68 | F | SEQUELA OF CEREBRAL INFRACTION | + | − | 13 | | 13 | |
| 583 | 82 | F | DEMENTIA | − | − | | | | |
| 584 | 89 | F | SEQUELA OF CEREBRAL INFRACTION | + | − | 1 | | 2 | |
| 588 | 91 | F | SEQUELA OF CEREBRAL INFRACTION | + | + | 15 | 10 | 15 | 10 |
| 589 | 84 | F | SEQUELA OF CEREBRAL INFRACTION | + | − | | | | |
| 594 | 87 | F | DEMENTIA | − | − | | | | |
| 595 | 68 | M | SEQUELA OF CEREBRAL INFRACTION | − | − | | | | |
| 596 | 64 | M | SEQUELA OF CEREBRAL HEMORRHAGE | + | − | 5 | | 8 | |

FIG.6

FIG.7

ENTERAL NUTRITION PRODUCT AND METHOD FOR PREPARING THE SAME

CROSS-REFERENCE TO RELATED APPLICATIONS

This application is based on Japanese Patent Applications No. 2001-323124 filed Oct. 22, 2001 and No. 2002-108094 filed Apr. 10, 2002, and International Application PCT/JP02/10704 filed Oct. 15, 2002, the contents of which are incorporated hereinto by reference.

This is a continuation of International Application PCT/JP02/10704 filed Oct. 15, 2002, which was published in Japanese under PCT Article 21(2).

BACKGROUND OF THE INVENTION

1. Field of the Invention

The present invention relates to an enteral nutrition product for administration to a patient via a tube for nourishment, and more specifically to improvements in techniques for suppressing or reducing gastro-esophageal reflux that causes an administered enteral nutrition product to regurgitate from the stomach toward the esophagus of a patient.

2. Description of Related Art

Several approaches for feeding nutrition to patients are known. These approaches are classified as enteral feeding and transvenous feeding, according to the organ or region of the human body to which nutrition is fed. While enteral feeding is a procedure for administrating nutrition to the intestines, transvenous feeding is a procedure for administrating nutrition to blood flowing in the central or peripheral veins of a patient. Enteral feeding is classified into oral feeding and tube feeding, according to the route along which nutrition is fed from the outside to the inside of the body.

Oral feeding is conducted for a patient who can swallow food and allows such a patient to take food orally. Alternatively, tube feeding is conducted for a patient who suffers from dysphagia, by feeding nutrition to the patient's stomach or intestines via a feeding tube. Nutrition for administration by tube feeding is referred to as an enteral nutrition product. That is, tube feeding is a procedure for administering an enteral nutrition product to a patient via a tube, and it is classified into nasogastric tube feeding, gastrostomy feeding, and trans-intestinal-fistula feeding for feeding nutrition via a stoma formed in the intestines.

The above nasogastric tube feeding is conducted by intubating a feeding tube into the esophagus of a patient, with the feeding tube being open at one end positioned in the patient's mouth or nose, and then feeding an enteral nutrition product via the feeding tube into the stomach or intestines.

Alternatively, gastrostomy feeding is conducted by inserting a feeding tube through a stoma formed through the abdominal and stomach walls of a patient, and then feeding an enteral nutrition product from outside of the body to the inside of the stomach via the feeding tube. In addition, the above trans-intestinal-fistula feeding is a procedure to be conducted by inserting a feeding tube through a stoma formed through the abdominal and intestinal walls of a patient, and then feeding an enteral nutrition product from the outside of the body to the inside of the intestines via the feeding tube.

Japanese Publication No. JP2000-152975 discloses a conventional technique of administering an enteral nutrition product in the form of a fluid diet to a patient in a transnasal (i.e., via nose) or percutaneous (i.e., via skin) manner.

Japanese Publication for republishing in Japanese International Publication WO 00/13529 discloses a conventional technique of administering an anti-vomiting food which is made of a liquid solution containing a thickener, to a patient who is expected to undergo a transluminal (i.e., via a tube) administration of an enteral nutrition product in the form of a fluid diet, before, after or during the administration of the anti-vomiting food to the patient via a tube.

As for matters that demand attention in an attempt to administer an enteral nutrition product to a patient, suppression or reduction of gastro-esophageal reflux is referred to. The reason is that gastroesophageal reflux can be a cause of reflux esophagitis, aspiration pneumonitis, etc. While reflux esophagitis is an esophagitis resulting from the stimulation of the gastric acid within the contents regurgitated from the stomach, aspiration pneumonitis is pneumonitis due to the invasion of the regurgitated contents into the trachea.

The cardia has been formed in the stomach so as to function as a lid for preventing a gastric regurgitation toward the esophagus. In case of elderly people who require the above enteral feeding, in general, the function of the cardia is deteriorated, and however, even if the function of the cardia is normal, it is highly possible that gastro-esophageal reflux will occur. Therefore, when the administration of an enteral nutrition product to an aged patient is needed, the prevention of gastro-esophageal reflux is strongly demanded.

However, not only where a liquid enteral-nutrient but also where a fluid enteral nutrition product is used according to the disclosure of the aforementioned Japanese Publication JP2000-152975, gastro-esophageal reflux failed to be reduced adequately. As a result, a heavy burden was imposed on a caregiver for a patient.

Figure 5:
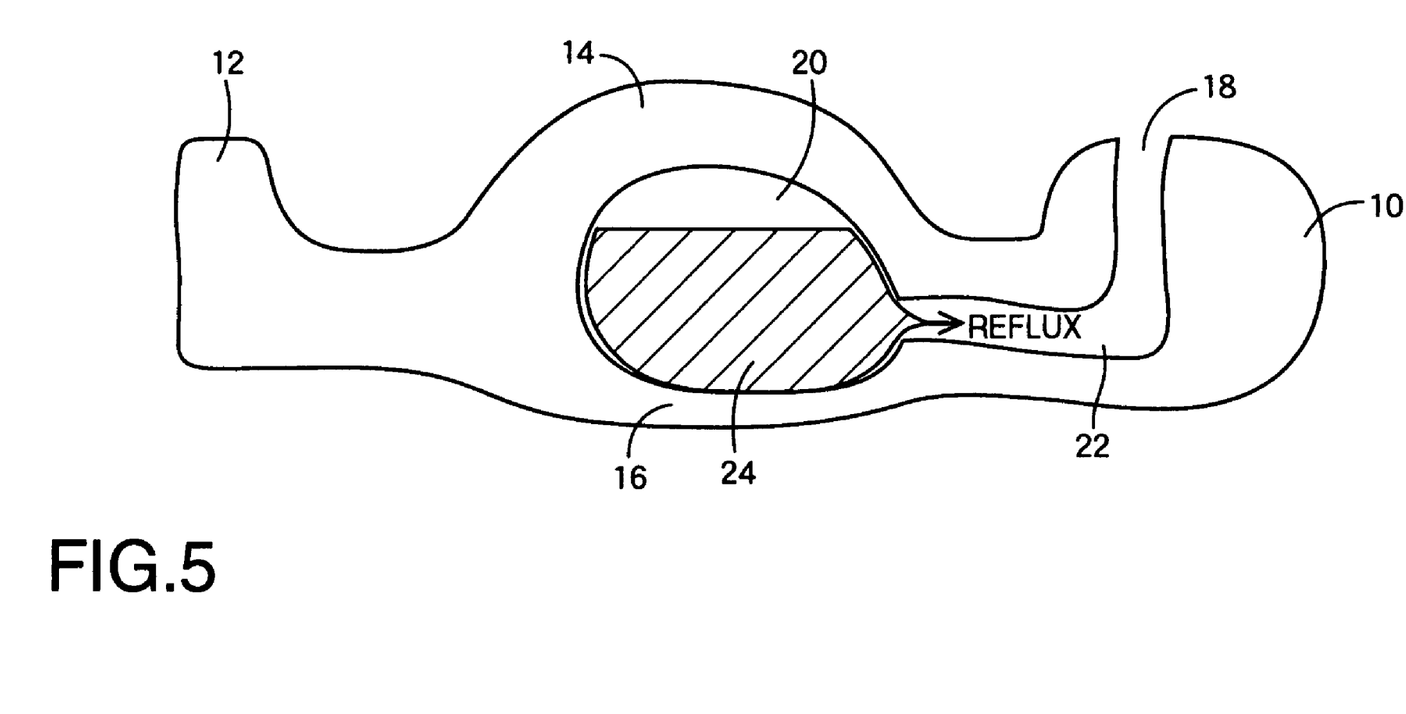
FIG. 5 is a side view in section illustrating a model for explaining how easily gastro-esophageal reflux of a conventional enteral nutrition product 24 in a liquid or fluid state occurs in a condition that the enteral nutrition product 24 has been administered via a tube to a patient in a supine position.

FIG. 5 illustrates a model for explaining that, when a liquid or fluid enteral nutrition product is administered to a patient via a tube, there is a strong tendency for the enteral nutrition product to regurgitate from the stomach toward the esophagus. In FIG. 5, numeral reference 10 denotes the head of a patient, 12 denotes the feet, 14 denotes the abdomen, 16 denotes the back, 18 denotes the mouth, 20 denotes the stomach, 22 denotes the esophagus, and 24 denotes a liquid or fluid enteral nutrition product.

In addition, if the conventional technique disclosed in the aforementioned Japanese Publication for republishing in Japanese International Publication WO 00/13529 is practiced, it appears to be possible that both the fluid diet serving as the enteral nutrition product and the thickener, after being mixed together within the stomach of a patient, react with each other in a proper manner, and that, after a rise in viscosity of the contents of the stomach as a result of the reaction, gastro-esophageal reflux is reduced.

However, before the reaction between the fluid diet and the thickener occurs, both the fluid diet and the thickener are lower in viscosity. Thus, there arises a period of time during which the fluid diet and the thickener are stayed within the patient's body at a lower viscosity, and, as a result, it is highly possible that gastro-esophageal reflux will occur.

Therefore, even if the above-mentioned conventional technique is carried out, it is difficult to prevent gastro-esophageal reflux in an appropriate manner throughout the whole period of a process of administering the fluid diet and the thickener to a patient, ranging from the beginning to the end of the process.

SUMMARY OF THE INVENTION

With the foregoing circumstances in mind as a background, it is an object of the present invention to provide an enteral nutrition product allowing for an easy suppression or reduction of reflux of the enteral nutrition product from the stomach toward the esophagus once the enteral nutrition product is administered to the patient via a tube.

The object mentioned above may be achieved according to any one of the following modes of this invention. These aspects will be stated below such that these modes are sectioned and numbered, and such that these aspects depend upon the other aspects or modes, where appropriate. This is for a better understanding of some of a plurality of technological features and a plurality of combinations thereof disclosed in this description, and does not mean that the scope of these features and combinations is interpreted to be limited to the scope of the following aspects of this invention.

According to a first aspect of the present invention, an enteral nutrition product is provided for administration to the stomach or intestines of a patient via a feeding tube, from a container which is connected to a portion of the feeding tube outside the patient, upon application of pressure of the container, the feeding tube been placed through a through-hole of a stoma formed through an abdominal wall and a stomach wall of the patient, wherein the enteral nutrition product is formed as a semi-solid having approximately the same hardness as a pudding or a Japanese pot-steamed hotchpotch called CHAWAN-MUSHI, by adding agar or a whole egg as a semi-solidifying agent to a nutrient solution, the semi-solid being common to a solid in that the semi-solid has a shape retentivity allowing a shape of the semi-solid to be retained without a spontaneous change in shape, and in that the semi-solid is capable of containing a nutrition component at a higher concentration than those of a liquid and a fluid, the semi-solid being common to the liquid and the fluid in that the semi-solid is easier to be changed in shape due to an externally forced load than the solid, and wherein the shape retentivity is maintained before, during, and after administration of the enteral nutrition product into the patient, and is maintained while the enteral nutrition product is stayed within the stomach or the intestines of the patient, such that the enteral nutrition product is not liquefied due to a body temperature of the patient.

This enteral nutrition product according to the first aspect of the present invention has the characteristics equivalent to both those of a fluid liquid and those of a solid. As a result, while this enteral nutrition product has a shape retentivity allowing the shape of this enteral nutrition product to be retained without a spontaneous change in shape, this enteral nutrition product is easier to be changed in shape due to an externally forced load than a solid.

Further, this enteral nutrition product is prepared or manufactured as a semi-solid which is different from a liquid and a fluid in that the semi-solid bears a shape retentivity allowing the shape of the semi-solid to be retained without a spontaneous change in shape, and therefore, this enteral nutrition product would allow for an easier increase in viscosity or hardness, compared with those liquid and fluid.

In the regard, the "shape retentivity" may be defined as a characteristic allowing the initial shape of this enteral nutrition product to attempt to retain against gravity and atmospheric pressure that apply externally spontaneously on this enteral nutrition product.

Figure 4:
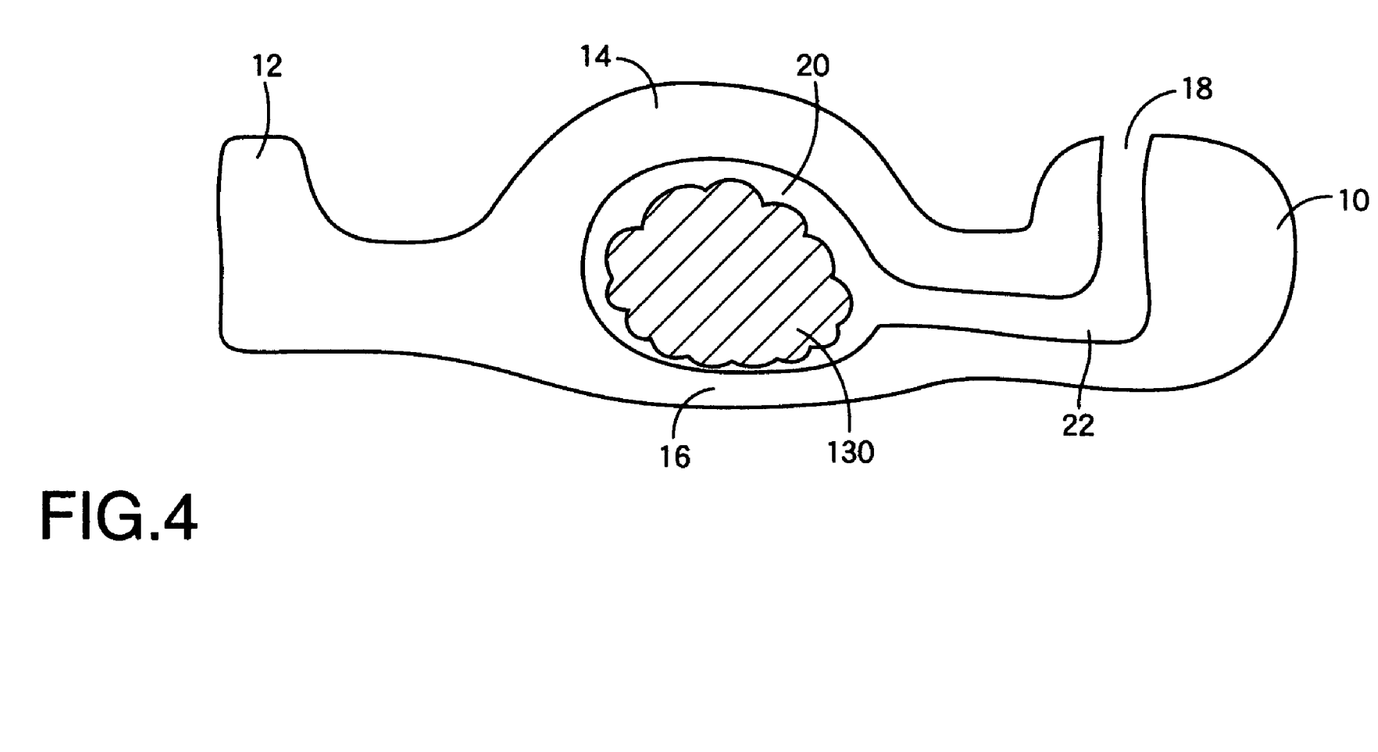
FIG. 4 is a side view in section illustrating a model for explaining how gastro-esophageal reflux of the enteral nutrition product 130 according to the first embodiment is reduced in a condition that the enteral nutrition product 130 has been administered via a tube to a patient in a supine position.

Therefore, the enteral nutrition product according to the first aspect of the present invention would result in, as shown in FIG. 4, an easier suppression or reduction of gastro-esophageal reflux occurring such that the enteral nutrition product 130 that was administered to a patient and is stayed within the stomach 20 regurgitates toward the esophagus 22.

The reduction of gastro-esophageal reflux of an enteral nutrition product would make it unnecessary to keep a patient in a sitting position during administration of the enteral nutrition product, for example. As a result, for the benefit of a patient, the possibility is reduced of causing bedsores at the buttock, the back, etc., of a patient, each of which exhibits a higher contact pressure, during administration of an enteral nutrition product.

When, due to a higher possibility of the use of a certain enteral nutrition product to cause gastro-esophageal reflux of a patient, there is a higher possibility that the patient will vomit due to the gastroesophageal reflux, a caregiver for the patient must keep close watch on the patient so that the caregiver may detect a sudden change in the patient's condition due to vomiting, if any, immediately after the occurrence of the sudden change. Because of that, a heavy observation burden is imposed on the caregiver.

However, the reduction of the possibility of gastro-esophageal reflux to occur with regard to an enteral nutrition product that was administered to a patient would reduce the caregiver's observation burden to watch the patient, which would also benefit the caregiver.

In the event where the conventional technique disclosed in the aforementioned Japanese Publication for republishing in Japanese International Publication WO 00/13529 is practiced, as previously described, during feeding of the fluid diet and the thickener to a patient, a rise in viscosity of the fluid diet by the thickener fails to occur, and accordingly, a higher possibility exists of an underviscosity period during which the viscosity of the contents in the stomach is lower than that at which gastro-esophageal reflux is difficult to occur, and also a higher possibility exists of gastro-esophageal reflux to occur in the underviscosity period.

Alternatively, the enteral nutrition product according to the first aspect of the present invention would allow for maintenance of the shape retentivity before, during, and after administration of the present enteral nutrition product to the body of a patient, with the result that the aforementioned underviscosity period is absent during administration of the present enteral nutrition product, and therefore, the reduction of gastro-esophageal reflux becomes easier to be achieved throughout the period of administering the present enteral nutrition product.

Further, in the event where the conventional technique disclosed in the aforementioned Japanese Publication for republishing in Japanese International Publication WO 00/13529 is practiced, it is highly possible that the total volume of the fluid diet and the thickener, which is expected to be totally fed to a patient, is larger than the total volume of a semi-solid enteral-nutrition product. The reason is that, as previously described, the thickener is a liquid, and as a result, the mixture of the thickener and the fluid diet contains more water than a semi-solid enteral-nutrition product.

On the other hand, the enteral nutrition product according to the first aspect of the present invention is formed as a semi-solid that is common to a solid in that the semi-solid is capable of containing a nutrient at a higher concentration than a liquid and a fluid.

Therefore, this enteral nutrition product would allow for an easier reduction of the total volume of substances that are expected to be totally fed to a patient, resulting in an easier reduction in the time required for administration of this enteral nutrition product. The reduction in the time required for administration would lead to reduction of the burden of the patient and a caregiver for the patient, with the effect that both a tendency of bacteria to enter and contaminate an enteral nutrition product, and a tendency of the entered bacteria to proliferate are reduced, and therefore, it becomes easier to improve the cleanliness or purity of an enteral nutrition product for administration to a patient.

This enteral nutrition product changes in shape because of the segmentation of this enteral nutrition product due to an externally forced load. On the other hand, this enteral nutrition product is changed in its entire shape because of the segmentation of this enteral nutrition product due to an externally forced load applied from a feeding tube during passing of this enteral nutrition product through the feeding tube, and then, this enteral nutrition product is administered to a patient. Therefore, this enteral nutrition product exists in the human body in divisions. However, each division of this enteral nutrition product which is generated as a result of the above segmentation still bears the aforementioned shape retentivity, and therefore, this enteral nutrition product in divisions also exhibits as a whole the shape retentivity more strongly than a liquid and a fluid.

That is, in this enteral nutrition product, the shape retentivity is maintained before, during, and after administration to a patient's body via a feeding tube.

Further, in this enteral nutrition product, the shape retentivity is maintained while this enteral nutrition product is stayed within a patient's body, such that this enteral nutrition product is not liquefied due to a body temperature of the patient.

In addition, for a food that a patient takes orally for nourishment, the food is required to be liquefied to a certain extent when taken into the mouth, for fostering the patient's swallowing. However, the contrary liquefaction enhances the possibility that gastro-esophageal reflux will occur.

On the other hand, since an enteral nutrition product is not a food which is taken orally, there is no need for preparing or manufacturing the enteral nutrition product so as to be liquefied upon administration.

Based on these findings, this enteral nutrition product according to the first aspect of the present invention is formed as a semi-solid bearing the above shape retentivity such that this enteral nutrition product is not liquefied owing to the body temperature of a patient.

Therefore, this enteral nutrition product would allow for an easier reduction of gastro-esophageal reflux without interfering the administration to a patient.

In general, as an enteral nutrition product exhibits stronger shape retentivity, its fluidity is decreased, i.e., the freedom of change in shape of the enteral nutrition product loses, and this means that the enteral nutrition product can become a factor inhibiting the enteral nutrition product from passing through a feeding tube. However, this enteral nutrition product according to the first aspect of the present invention is fed to the stomach or intestines of a patient via a feeding tube inserted into the body of the patient, from a container which is connected to a portion of the feeding tube outside the body of the patient, by employing a pressurization function of the container. Accordingly, this enteral nutrition product would make it easier to pass smoothly through a feeding tube, irrespective of the above shape retentivity exhibited more strongly than a liquid and a fluid.

The "enteral nutrition product" according to the first aspect of the present invention may be used under the aforementioned nasogastric tube feeding, gastrostomy feeding, or trans-intestinal-fistula feeding.

The "enteral nutrition product" according to the first aspect of the present invention may be prepared in the form of the aforementioned semi-solid by adding a semi-solidifying agent to a nutrient solution. In this case, white of egg, agar (gelatin made from seaweed), gelatin or other material, or an appropriate combination thereof may be selected as the semi-solidifying agent.

The "container" in the first aspect of the present invention does not matter with respect to any physical configuration taken by the "container," provided that the container has both the function of accommodating an enteral nutrition product in a semi-solid state, and the function of injecting into a feeding tube the enteral nutrition product accommodated in the container, by pressurizing the enteral nutrition product.

Therefore, the "container" may be a syringe where a plunger is fitted into a cylinder in an air-tight and slidable manner, or may be a flexible bag. The bag may be formed with film, such as aluminum film, synthetic resin film, etc., or may be formed to be of a closed-type for the purposes including the prevention of invasion of bactericidal, etc.

Additionally, the "container" may be of a first type allowing an enteral nutrition product to be principally stored only during its administration, in face of the timing of actually administering the enteral nutrition product, or may be of a second type allowing an enteral nutrition product to be stored prior to and during an actual administration of the enteral nutrition product, irrespective of the timing of the actual administration.

In the regard, where the above first type is adopted, an enteral nutrition product, prior to the administration, is transferred from a holder exclusively storing the enteral nutrition product to the above "container," and then, is fed from the container to a patient.

According to a second aspect of the present invention, the enteral nutrition product according to the first aspect is provided, wherein the enteral nutrition product is prepared by filling a holder, which is the same as the container or which is separate from the container, with a nutrient solution and by performing a predetermined semi-solidification process for the nutrient solution within the holder.

This enteral nutrition product according to the second aspect of the present invention exhibits the aforementioned shape retentivity both before and after the administration to the patient's body. Assuming that a holder is attempted to be filled with such a semi-solid enteral-nutrition product, it may be that, due to the shape retentivity of the enteral nutrition product, i.e., the characteristic of the semi-solid, the filling with the enteral nutrition product is not conducted smoothly.

By contrast, the enteral nutrition product according to the second aspect of the present invention changes from a liquid state before being filled into the holder into a semi-solid state only after the filling. As a result, this enteral nutrition product would make it easier to fill the holder more smoothly.

In this regard, the "holder" in the second aspect of the present invention may be the container in the previous first aspect, namely, the same as a container functioning to feed an enteral nutrition product into a feeding tube, with the container being connected with the feeding tube, or may be separate from the container.

The case where the "holder" is the same as the container in the previous first aspect corresponds to the case where the aforementioned first or second type is adapted. To the contrary, the case where the "holder" is separate from the container in the previous first aspect corresponds to the case where the "holder" means a storage which exclusively stores an enteral nutrition product, prior to an actual later administration of the enteral nutrition product, regardless of the timing of the actual later administration, but which does not store the enteral nutrition product during the actual later administration.

According to a third aspect of the present invention, the enteral nutrition product according to the second aspect is provided, wherein the enteral nutrition product is prepared by the steps including:

a step of adding a semi-solidifying agent to the nutrient solution;

a step of filling the holder with the nutrient solution to which the semi-solidifying agent has been added; and a step of performing the pre-determined semi-solidification process for the nutrient solution within the holder.

According to a fourth aspect of the present invention, the enteral nutrition product according to the third aspect is provided, wherein the semi-solidifying agent comprises at least white of egg among yellow and the white of egg of a hen. One example of the "at least white of egg" means the whole egg containing both yellow and white of egg of a hen.

According to a fifth aspect of the present invention, the enteral nutrition product according to the fourth aspect is provided, wherein the processing step comprises a heating step of heating the nutrient solution within the holder to perform the pre-determined semi-solidification process.

The "heating step" according to the fifth aspect may include, for example, a step of steaming or braising a mixture of the at least white of egg and the nutrient solution (including a fluid nutrient, if desired). In this regard, the "steaming," as one example of cooking, may be defined as heating of a material via steam. On the other hand, the "braising," as another example of cooking, may be defined as a direct heating of a material in parallel with heating of the same material via steam.

According to a sixth aspect of the present invention, the enteral nutrition product according to the third aspect is provided, wherein the semi-solidifying agent comprises agar.

According to a seventh aspect of the present invention, the enteral nutrition product according to the sixth aspect is provided, wherein the adding step comprises a heating step of heating a mixture of the nutrient solution and the agar such that the agar is dissolved into the nutrient solution, and wherein the processing step comprises a removing step of removing heat from the nutrient solution within the holder to perform the pre-determined semi-solidification process.

According to an eighth aspect of the present invention, the enteral nutrition product according to any one of the first through seventh aspects is provided, wherein the feeding tube is used so as to be intubated through the stoma formed through the abdominal and the stomach or intestinal wall of the patient, and wherein is larger in internal diameter and shorter in length than a feeding tube which is used so as to be inserted orally from a mouth or nose through an esophagus into the stomach, of the patient.

When the enteral nutrition product according to any one of the preceding first through seventh aspects is used under the aforementioned gastrostomy feeding or trans-intestinal-fistula feeding, a feeding tube through which the enteral nutrition product is required to pass, which is to say, a route along which the enteral nutrition product is administered, is not required to be longer than when the enteral nutrition product is used under the aforementioned nasogastric tube feeding.

Accordingly, the use of the enteral nutrition product according to any one of the preceding first through seventh aspects under the gastrostomy feeding or the trans-intestinal-fistula feeding would result in an easier reduction of the time required for administering a batch of the enteral nutrition product, coupled with the fact that the enteral nutrition product is not a liquid but a semi-solid which is easier in reducing a volume of the semi-solid which can contain the same amount of a nutrient.

Further, the fact that there is no need to shorten the aforementioned route for administration of an enteral nutrition product contributes to the capability of more easily preventing the enteral nutrition product from clogging a feeding tube and from eventually residing in the feeding tube during administration of the enteral nutrition product due to a higher viscosity of the enteral nutrition product.

Furthermore, in general, a feeding tube which is used so as to be intubated through a stoma formed through the abdominal wall and the stomach or intestinal wall of a patient is shorter in length and also larger in internal diameter than a feeding tube which is used so as to be intubated from the mouth or nose through the esophagus into the stomach, of a patient.

Then, when an enteral nutrition product is administered to a patient via a tube, the dependence on a shortened and dilated route of administration of an enteral nutrition product would result in an easier reduction in the time required for administration, and additionally, would result in an easier avoidance of a resided enteral nutrition product within a feeding tube.

Based on these findings, the enteral nutrition product according to the eighth aspect of the present invention is defined as an enteral nutrition product which is used so as to be fed from the outside of a human body through a feeding tube which has been inserted through a through-hole of a stoma formed through the abdominal wall and the stomach or intestinal wall of the patient into the stomach or intestines. That is, this enteral nutrition product is used under the aforementioned gastrostomy feeding or the trans-intestinal-fistula feeding.

When an enteral nutrition product is required to be administered to a patient through a gastric fistula formed through the abdominal and the stomach wall, if a feeding tube extending from the gastric fistula into the intestines (hereinafter, referred to as "gastrostomy jejunum tube") is not used, the enteral nutrition product is fed into the stomach, and then, the enteral nutrition product is fed into the intestines due to the peristalsis of the stomach. By contrast, if the gastrostomy jejunum feeding tube is used, the enteral nutrition product is directly fed into the intestines without feeding of the stomach. Such a feeding may be referred to as gastrostomy jejunum feeding.

The enteral nutrition product according to the eighth aspect of the present invention may be used under the gastrostomy jejunum feeding.

In general, in order to satisfy a need for a smooth passing of the enteral nutrition product through a feeding tube, a given constraint may be imposed between the degree of the aforementioned shape retentivity of the enteral nutrition product and the internal diameter of the feeding tube. The constraint means that the more strongly the enteral nutrition product shows the shape retentivity, the larger the internal diameter of the feeding tube is required to become, for improving the freedom of change in shape of the enteral nutrition product within the feeding tube.

To the contrary, the enteral nutrition product according to the eighth aspect of the present invention is defined as an enteral nutrition product which is administered to a patient via a feeding tube used under the aforementioned gastrostomy feeding and trans-intestinal-fistula feeding. The feeding tube is larger in internal diameter than a feeding tube used under the aforementioned nasogastric feeding.

Therefore, this enteral nutrition product would make it more easily to be administered to a patient via a feeding tube with a larger internal diameter, irrespective of the aforementioned shape retentivity which this enteral nutrition product exhibits more strongly than a liquid and a fluid.

According to a ninth aspect of the present invention, an enteral nutrition product with a container is provided, the enteral nutrition product being for administration into a patient via a tube, wherein the enteral nutrition product is formed as a semi-solid being common to a solid in that the semi-solid has a shape retentivity allowing a shape of the semi-solid to be retained without a spontaneous change in shape, and in that the semi-solid is capable of containing a nutrition component at a higher concentration than those of a liquid and a fluid, the semi-solid being common to the liquid and the fluid in that the semi-solid is easier to be changed in shape due to an externally forced load than the solid, wherein the shape retentivity is maintained before, during, and after administration of the enteral nutrition product into the patient, and is maintained while the enteral nutrition product is stayed within the patient, such that the enteral nutrition product is not liquefied due to a body temperature of the patient, and wherein the enteral nutrition product is prepared by:
filling the container with a nutrient solution; and
performing a predetermined semi-solidification process for the nutrient solution within the container.

This with-container enteral nutrition product according to the ninth aspect provides the same effects, based on the same principle, as those of the enteral nutrition product according to the first aspect.

When a comparison is made between a first case where a container is attempted to be filled with an enteral nutrition product in a liquid state, and a second case where the same container is attempted to be filled with the same enteral nutrition product in a semi-solid state, it is more likely in the second case than in the first case that, due to the shape retentivity of the enteral nutrition product (i.e., a characteristic of a semi-solid), the filling of the container fails to be conducted efficiently. The likelihood is increased, as the shape retentivity of the enteral nutrition product becomes stronger, and as an opening of the container becomes smaller in diameter.

In contrast, the with-container enteral nutrition product according to the ninth aspect is changed in state from a liquid state before filling of the container, into a semi-solid state only after filling of the container. Therefore, this with-container enteral nutrition product would facilitate an efficient filling of the container.

The "container" in the ninth aspect may be of a type allowing an enteral nutrition product to be principally stored only during its administration, in face of the timing of actually administering the enteral nutrition product, and allowing, in connection with a feeding tube, the enteral nutrition product to be injected into the feeding tube. Further, the "container" may be of a type allowing an enteral nutrition product to be stored prior to and during an actual administration of the enteral nutrition product, irrespective of the timing of the actual administration, and allowing, in connection with a feeding tube, the enteral nutrition product to be injected into the feeding tube.

Furthermore, the "container" in the ninth aspect may be of a type in which, irrespective of the timing of an actual later administration of an enteral nutrition product, the enteral nutrition product is stored before the actual later administration but is not stored during the actual later administration.

In addition, the "container" in the ninth aspect does not matter with respect to any physical configuration taken by the "container," provided that the container has at least the former one of the function of accommodating an enteral nutrition product in a semi-solid state, and the function of injecting into a feeding tube the enteral nutrition product accommodated in the container, by pressurizing the enteral nutrition product.

Therefore, the "container" may be a syringe where a plunger is fitted into a cylinder in an air-tight and slidable manner, or may be a flexible bag. The bag may be formed with film, such as aluminum film, synthetic resin film, etc., or may be formed to be of a closed-type for the purposes including the prevention of invasion of bactericidal, etc.

The enteral nutrition product according to the ninth aspect may be used in combination with a technical feature set forth in any one of the preceding first through eighth aspects.

According to a tenth aspect of the present invention, a syringe which is filled with the enteral nutrition product defined in any one of the first through eighth aspects and which pressurizes and injects the enteral nutrition product, thereby to administer the enteral nutrition product to the patient, wherein the syringe is commercialized together with the enteral nutrition product, such that the syringe has been previously filled with the enteral nutrition product, whereby the syringe functions as a container for containing the enteral nutrition product, prior to use of the syringe.

The administration of the enteral nutrition product according to any one of the preceding first through eighth aspects to a patient using a feeding tube requires forcing of the enteral nutrition product through the feeding tube so as to exceed the aforementioned shape retentivity or the viscosity of the enteral nutrition product. This forcing can be performed by pressurizing the enteral nutrition product using a syringe so as to administer the enteral nutrition product to a patient.

As described above, when an approach is selected of administering an enteral nutrition product to a patient using a syringe, wherein the approach can be referred to as forced administration to the effect that the approach is distinguished from a spontaneous or natural administration in which the administration is achieved by employing a natural drop of a substance, it is general that an enteral nutrition product and an syringe are commercialized separately from each other, and that the enteral nutrition product is transacted in a state that the enteral nutrition product is reserved in an exclusive container.

As described previously, when an enteral nutrition product and a syringe are individually commercialized, the enteral nutrition product, prior to the administration, suctioned using the syringe from an exclusive container containing the enteral nutrition product, and as a result, a chamber of the syringe is filled with the enteral nutrition product. Then, a plunger of the syringe is pressed into a cylinder of the syringe, and as a result, the enteral nutrition product is fed from the chamber into a patient.

Alternatively, the syringe according to the tenth aspect is commercialized, after the syringe has been filled with an enteral nutrition product, in the form of a unitary product incorporating the enteral nutrition product, whereby the syringe functions, prior to the use, as a container containing the enteral nutrition product. This syringe can be referred to as pre-filled type.

Therefore, this syringe according to the tenth aspect would remove, prior to administration of an enteral nutrition product, a need of pouring the enteral nutrition product from an exclusive container into the syringe, resulting in a simplified procedures required for administration, and in an easier reduction in the time required for administration.

DETAILED DESCRIPTION OF THE INVENTION

The preferred embodiments according to the present invention are described below in more detail with reference to the drawings.

Figure 1:
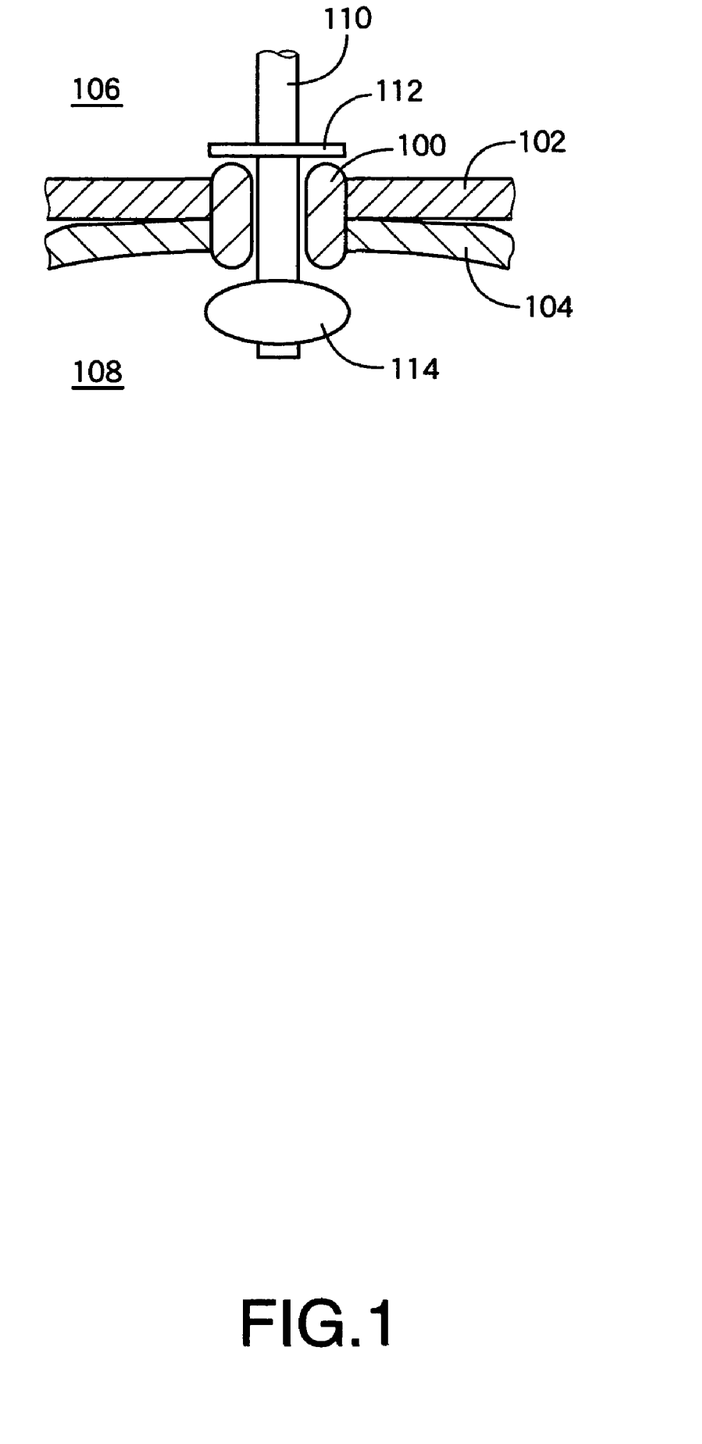
FIG. 1 is a partial cross-section side view illustrating a gastric fistula 100 and a gastrostomy tube 110 used to administer an enteral nutrition product to a patient via a tube according to a first embodiment of the present invention.

An enteral nutrition product according to a first embodiment of the present invention is used for administration to the stomach of a patient via a gastric fistula formed in the patient. That is, this enteral nutrition product is used under the aforementioned gastrostomy feeding. As shown in FIG. 1, a gastric fistula 100 is formed through an abdominal wall 102 and a stomach wall 104 of the patient, such that the gastric fistula 100 communicates each other an outer space 106 and an inner space 108 with regard to the patient.

While the gastric fistula 100 can be formed by laparotomy, it can be also percutaneously formed using an endoscope inserted into the stomach. The latter process, namely, Percutaneous Endoscopic Gastrostomy (PEG) is, more specifically, a process of inserting a tube from the outside of a patient into the stomach using an endoscope, and of forming a gastric fistula at the abdominal and stomach wall of the patient around the tube.

It has been said that this Percutaneous Endoscopic Gastrostomy (PEG) is more advantageous than the formation of a gastric fistula by laparotomy in that the performance of this PEG results in a fewer induced complications of a patient. In addition, it has been also said that, when the Percutaneous Endoscopic Gastrostomy (PEG) is performed, less pain is caused in a patient and also less burden or load is imposed on a caregiver, than when a feeding tube is inserted, for performing the aforementioned nasogastric feeding, into a patient such that the feeding tube passes through the nose and the esophagus and reaches the stomach. Because of such as the two reasons mentioned-above, the use of Percutaneous Endoscopic Gastrostomy (PEG) is rapidly increasing today.

When the gastrostomy feeding is conducted, as shown in FIG. 1, a gastrostomy tube or gastric fistula tube 110 functioning as a feeding tube is inserted through the gastric fistula 100. The gastrostomy tube 110 is positioned relative to the gastric fistula 100 using by an outer retaining member 112 and an inner retaining member 114 which have been attached to the gastrostomy tube 110.

The enteral nutrition product, after passing through the gastrostomy tube 110, is fed into the stomach from the outside of the body of a patient. The gastrostomy tube 110 is larger in lumen (larger in internal diameter) and is shorter in length, than a nasogastric feeding tube generally used as a feeding tube for performing the aforementioned nasogastric feeding. The general nasogastric tube is smaller in lumen (smaller in internal diameter), such as ranging from 2 through 4 [mm] in internal diameter, and is longer, such as exceeding 60 [cm].

Therefore, when an enteral nutrient is administered to a patient using a general nasogastric tube, the form of the enteral nutrient is desirably selected to be a liquid for ensuring easy-to-flow of the enteral nutrient. Alternatively, when an enteral nutrient is administered to a patient using the gastrostomy tube 110, easy-to-flow of the enteral nutrient can be ensured even if the form of the enteral nutrient is selected to be a semi-solid bearing the shape retentivity more strongly than a liquid.

Figure 2:
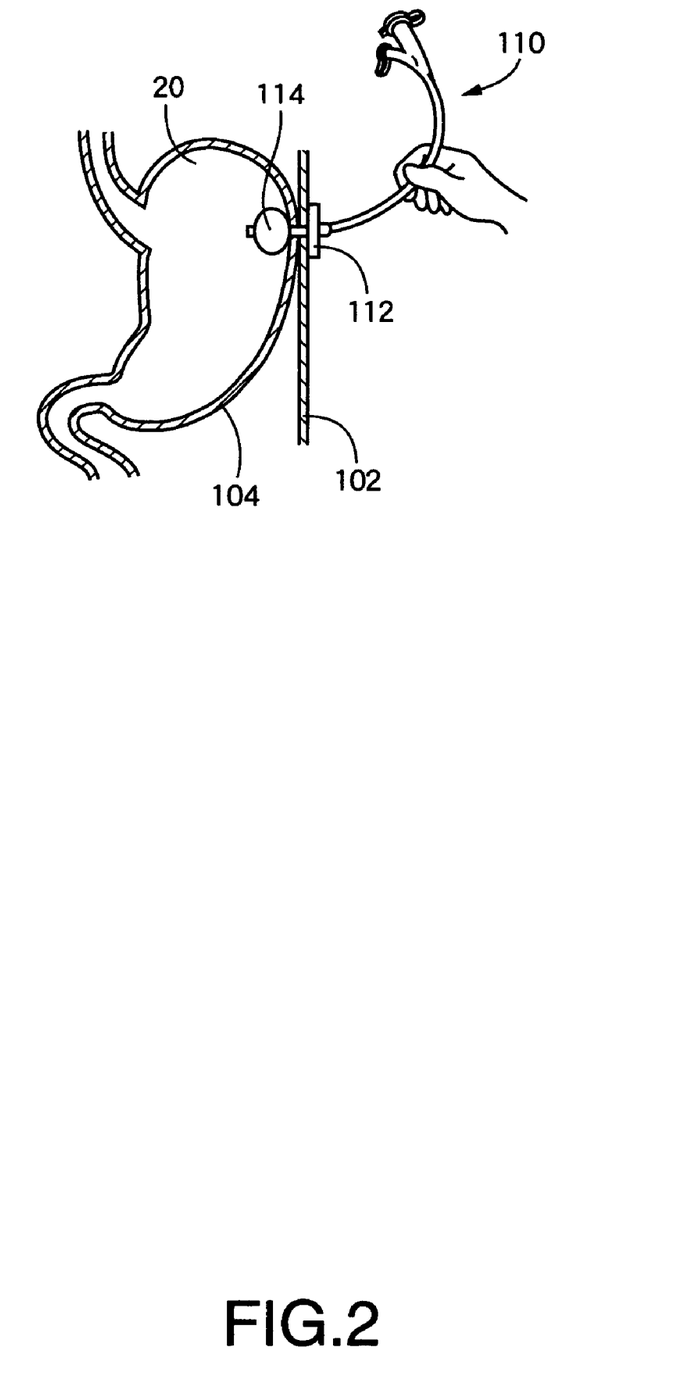
FIG. 2 is a side view partly in section illustrating the gastrostomy tube 110 along with a positional relationship with a stomach 20 and an abdominal wall 102.

FIG. 2 shows a positional relationship between the abdominal wall 102, the stomach wall 104, and the gastrostomy tube 110 in a side view partly in section.

Figure 3:
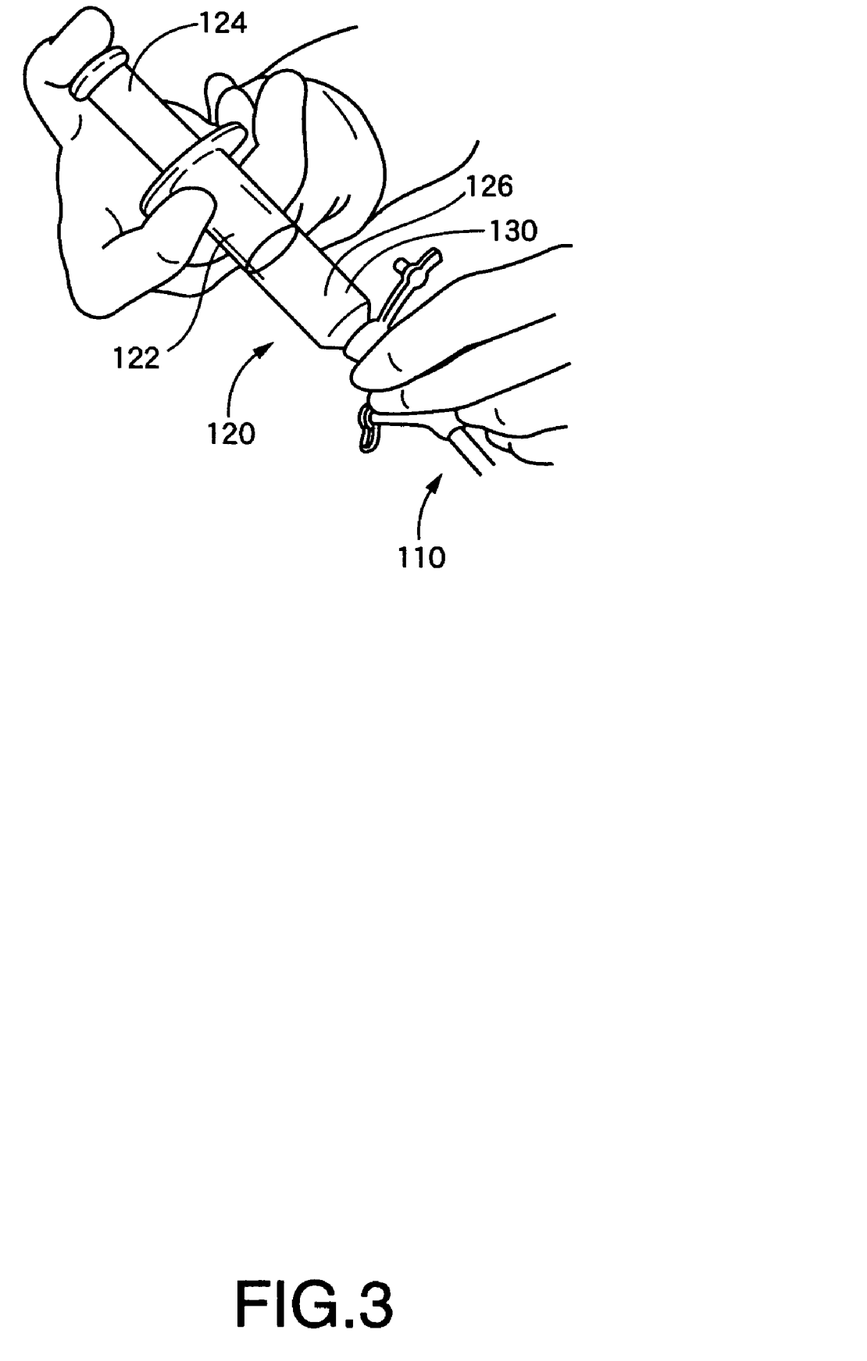
FIG. 3 is a perspective view illustrating a pre-filled syringe 120 which is commercialized in a state that the syringe 120 has been previously filled with an enteral nutrition product 130 according to the first embodiment.

As shown in FIG. 3, the enteral nutrition product according to the presently preferred embodiment is fed into the stomach 20 using a syringe 120. In the syringe 120, a plunger 124 is slidably fitted into a cylinder 122. A chamber 126 is formed between the cylinder 122 and the plunger 124 so as to be communicated with a nozzle of syringe 120 (invisible in concealment in FIG. 3). The chamber 126 has been filled with the enteral nutrition product 130 according to the presently preferred embodiment, wherein the enteral nutrition product 130 is expected to be injected by the syringe 120. In general, the nozzle of the syringe 120 is larger in diameter than that of a general syringe.

After the plunger 124 is pressed deeply into the cylinder 122, the filling enteral nutrition product 130 is injected into the gastrostomy tube 110, with the result that the enteral nutrition product 130 is fed through the gastrostomy tube 110 into the stomach 20 due to an externally forced load. Thus, the enteral nutrition product 130 is forced into the body of a patient for administration.

The enteral nutrition product 130 is prepared or manufactured as follows.

First, 250 [ml] of a nutrient solution (that is, a liquid containing nutrients to be administered to a patient) is provided in a container. Next, one raw whole egg is added into the nutrient solution and they are stirred. Then, a portion of a mixture of the nutrient solution and the raw whole egg is suctioned by the syringe 120, a capacity of which is 100 [ml], and then fills the chamber 126.

Following that, the syringe 120 which has been thus filled with the mixture is positioned in a given cooking device, and the mixture along with the syringe 120 is steamed or braised. Then, the enteral nutrition product 130 is completed.

The thus prepared enteral nutrition product 130 has been formed as a semi-solid. In the regard, the "semi-solid" is referred to a substance which is common to a solid in that the semi-solid has a shape retentivity allowing a shape of the semi-solid to be retained without a spontaneous change in shape, and in that the semi-solid is capable of containing a nutrition component at a higher concentration than those of a liquid and a fluid, and which is common to the liquid and the fluid in that the semi-solid is easier to be changed in shape due to an externally forced load than the solid. This enteral nutrition product 130 is made to be equivalent in viscosity and hardness to those of a pudding, a Japanese pot-steamed hotch-potch called CHAWAN-MUSHI in Japan, etc.

Therefore, as shown in FIG. 4, the administration of the enteral nutrition product 130 to a patient results in reduction of gastro-esophageal reflux causing the contents of the stomach 20, i.e., the enteral nutrition product 130 to regurgitate toward the esophagus 22, depending on the shape retentivity of the enteral nutrition product 130.

As a result, the present embodiment makes it inessential to keep a patient in a sitting position during the administration of the enteral nutrition product 130 to the patient, resulting in a capability of administering the enteral nutrition product 130 in a normal condition to a patient in a supine position which gives less pain to the patient, as shown in FIG. 4.

In addition, a whole egg in a steamed or braised state within a patient functions as a material preventing liquefaction due to a body temperature of the patient. Therefore, the enteral nutrition product 130 within a patient is inhibited from being liquefied due to the body temperature.

As is evident from the above, while, in the present embodiment, a whole egg is used in order to enhance the viscosity of the nutrient solution, the present invention may be carried out by the use of agar, for example, instead of a whole egg, excepting that the cooking of the enteral nutrition product 130 is easier when a whole egg is used than when agar is used.

Additionally, in the present embodiment, prior to steaming or braising of a mixture of a whole egg and a nutrient solution, the mixture is suctioned by the syringe 120 and then fills the syringe 120, and the mixture is steamed or braised along with the syringe 120. That is, the liquid mixture, after filling the syringe 120, is heated within the syringe 120, resulting in the semi-solidification of the mixture. Therefore, the present embodiment makes it easier to fill the syringe 120 having its smaller opening, with the semi-solid enteral-nutrition product 130.

However, the present invention may be carried out such that the enteral nutrition product 130, after being prepared through the steaming or braising of the liquid mixture, fills the syringe 120. Furthermore, in the present embodiment, the syringe 120 which has been filled with the enteral nutrition product 130 is commercialized and shipped as a unitary product.

As a result, the present embodiment removes a procedure of suctioning the enteral nutrition product 130 by the syringe 120 and filling the syringe 120, prior to administration of the enteral nutrition product 130 to a patient, resulting in reduction in labor and time required for administration of the enteral nutrition product 130.

A second embodiment of the present invention will be described below.

An enteral nutrition product according to the present embodiment is used so as to be administered via a gastric fistula formed in a patient, as is the case with the enteral nutrition product 130 according to the first embodiment. That is, this enteral nutrition product according to the present embodiment is used under the gastrostomy feeding as well.

While the enteral nutrition product 130 according to the first embodiment is prepared, as previously mentioned, by using a whole egg as a semi-solidifying agent, the enteral nutrition product according to the present embodiment is prepared by using agar as the semi-solidifying agent. The agar is a dried powder type.

Agar has been thus selected as the semi-solidifying agent for the following reasons:

(a) Agar is more easily accessible and cookable;

(b) Agar is capable of easily controlling the degree of semi-solidification, namely, the hardness of an enteral nutrition product;

(c) An enteral nutrition product that has been semi-solidified with agar is not dissolved (liquefied) within the body of a patient;

(d) Agar does not adversely affect a patient's health, because agar is lower in calories and contains more fiber; and (e) An enteral nutrition product that has been semi-solidified with agar is more easily fed into a patient through the gastrostomy tube 110, because of a lower consistency of the semi-solidified enteral-nutrition product.

In the present embodiment, for preparing the enteral nutrition product, a commercially available nutrient solution (that is, a liquid containing nutrient elements to be administered to a patient) is used. The nutrient solution is made to be a defined formula diet or a semi-digested diet. The nutrient solution, when its dilution is needed for reduction in a patient's caloric intake, etc., is mixed with a required amount of water (one example of a diluent solution). The mixture is then heated. Under the condition, powdered agar is added to the liquid mixture at a rate of 1 [g] per 200 [ml] of water. Following that, the agar is stirred and dissolved in the mixture.

Next, the mixture in which agar has been dissolved is in a liquid state, and the mixture in a liquid state is suctioned by and into the syringe 120 for filling the syringe 120.

Subsequently, the syringe 120 containing the liquid mixture is preserved in a cold location such as within a refrigerator. Accordingly, heat is removed from the liquid mixture is removed, resulting in solidification of the mixture owing to agar. That is, the mixture turns to be a semi-solid under the influence of agar, and therefore, the semi-solid enteral-nutrition product is completed under a condition that the syringe 120 has been previously filled with the enteral nutrition product. The degree of hardness of the enteral nutrition product is made to be equivalent to that of a pudding.

This enteral nutrition product is fed into the gastrostomy tube 110 using the syringe 120. In the present embodiment, a required amount of the enteral nutrition product per one batch of administration may be fed into a patient using the syringe 120 at a stroke, and the time required for administration amounts to only a few minutes.

The inventor of the present invention made clinical trials for respective patients in order to verify an effect of the enteral nutrition product to prevent gastro-esophageal reflux.

In the clinical trials, for each patient, the semi-solid enteral-nutrition product and a liquid enteral-nutrient were separately administered to the same patient for the respective two cases, and an assessment was made per case about whether gastro-esophageal reflux occurred or not. In cases where gastro-esophageal reflux occurred, based on images obtained via computed tomography (CT), the length of the region of the esophagus that was occupied by the regurgitated content of the stomach was measured (the distance between the upper end and the lower end of the regurgitated content), as well as the distance between the upper end of the regurgitated content and the cardia.

The computed tomography (CT) is performed for each patient, such that after 30 minutes elapsed from the time when an enteral nutrient (selectively meaning the liquid enteral-nutrient or the semi-solid enteral-nutrition product) containing contrast medium was administered to each patient, slice images of the thorax of each patient were picked up in a one-centimeter-width slicing manner. A determination was made of whether the contrast medium was present or not in each of the slice images picked up, in association with a CT value of each portion of the esophagus. The CT value is indicative of a height position of each portion of the esophagus, expressed by the number of slices. Depending on the results of the above determination, a determination was made of whether gastro-esophageal reflux occurred or not.

The above-defined enteral nutrient containing the contrast medium was prepared, regardless of whether it is a liquid or a semi-solid, by adding water-soluble contrast medium to the enteral nutrient at a rate of 5 [ml] per 100 [ml] of the enteral nutrient. The semi-solid enteral-nutrition product was semi-solidified after the addition of the contrast medium.

The above-defined enteral nutrient was administered to a patient, regardless of whether it is a liquid or a semi-solid, by 400 [ml] per batch of administration. The liquid enteral-nutrient was administered to a patient for 15 minutes for one batch of administration, and on the other hand, the semi-solid enteral-nutrition product was administered to a patient using the syringe 120, a capacity of which was 50 [ml], at a stroke.

Figure 6:
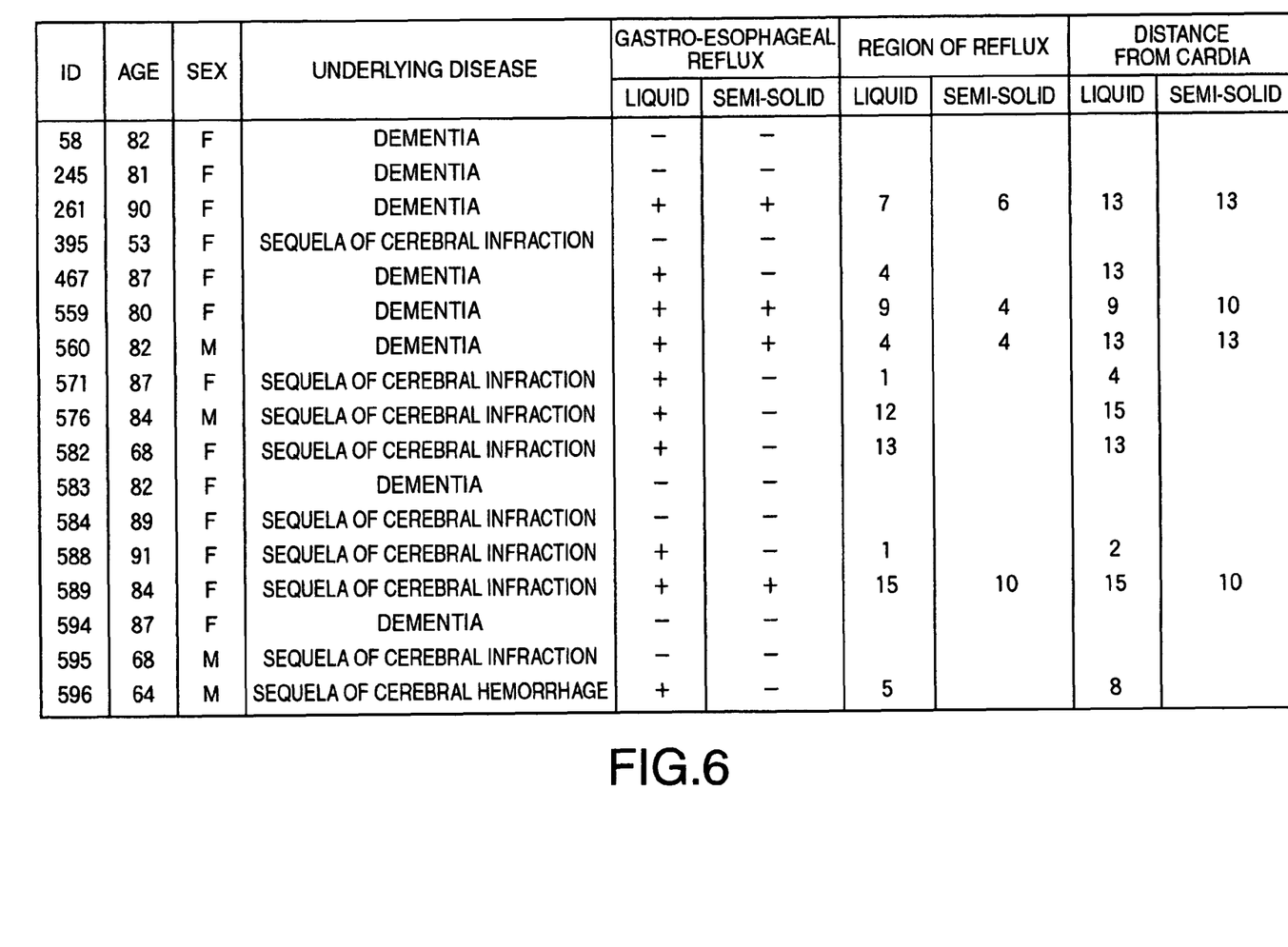
FIG. 6 is a table indicating the results of a clinical trial made for verification of an anti-gastroesophageal-reflux effect provided by an enteral nutrition product according to a second embodiment of the present invention, in comparison with those of a liquid enteral-nutrient.

FIG. 6 shows in a table the results of the current clinical trials. In FIG. 6, at the column indicating of whether gastro-esophageal reflux occurred or not, "−" denotes that gastro-esophageal reflux was negative, while "+" denotes that gastro-esophageal reflux was positive. In addition, the aforementioned length of the range of regurgitation and the aforementioned distance from the cardia were measured on the basis of the aforementioned CT values.

The current clinical trials were conducted for 17 patients. Although the patients were all bedridden, they were medically stable. In FIG. 6, the patients are identified respectively by their identification numbers, their ages and sexes are listed as their features, and their underlying diseases are also listed.

According to the results indicated in FIG. 6, it was recognized that 10 (58.5%) of 17 patients each exhibited gastro-esophageal reflux. On the other hand, it was recognized that 4 (23.5%) of those patients each exhibited gastro-esophageal reflux after administration of the semi-solid enteral-nutrition product.

Therefore, it was verified that the enteral nutrition product in accordance with the present embodiment reduces gastro-esophageal reflux better than the liquid enteral-nutrient.

The enteral nutrition product according to the present embodiment is more advantageous than the liquid enteral-nutrient for the following reason. That is, it has already been reported that a case exists in which the frequency of the occurrence of gastro-esophageal reflux is increased after the formation of the gastric fistula in a patient. Although the cause has not yet been definitely elucidated, the following indication has been provided with regard to the cause.

That is, the fixation of the stomach wall to the abdominal wall in preparation for the formation of a gastric fistula would suppress the peristalsis of the stomach, resulting in a declined excretory function of the stomach. It has already been indicated that a declined excretory function of the stomach brings about a long-time retention of the enteral nutrition product in the stomach, leading to an increased frequency of the occurrence of gastro-esophageal reflux.

On the other hand, the factors for fostering or repressing the gastric peristalsis associated with the gastric excretory function include, in addition to neural factors, humoral regulation factors which depend on various kinds of gastrointestinal hormone. There exists gastrin as one of the various kinds of gastrointestinal hormone which it has been said that stimulates the gastric peristalsis the most strongly. The secretion of gastrin is stimulated by stretch of the stomach wall.

When a liquid enteral-nutrient is administered to the stomach of a patient via a nasogastric tube, it is, in general, recommended that the liquid enteral-nutrient be dropped at a speed slow enough to avoid a patient from vomiting during the administration. However, it is impossible to impregnate the stomach with the liquid enteral-nutrient at such a slow speed, causing an insufficient stretch of the stomach due to the administration of the liquid enteral-nutrient. As a result, not only the secretion of gastrin but also the gastric peristalsis are inactive, resulting in a declined excretory function of the stomach, and eventually, gastro-esophageal reflux might be contrary fostered.

Alternatively, the present embodiment, since it allows the enteral nutrition product to be administered directly to the stomach through the gastric fistula, enables the enteral nutrition product to be administered into the stomach rapidly without fear of vomiting. Therefore, the stomach is largely stretched owing to the administration of the enteral nutrition product to the stomach, resulting in a stimulated secretion of gastrin, and therefore, an active gastric peristalsis can be expected. As a result, the excretory function of the stomach is improved, and the frequency of occurrence of gastro-esophageal reflux of the enteral nutrition product is favorably reduced, coupled with the enteral-nutrition product being a semi-solid.

After a gastric fistula has been formed in a patient, the phenomenon in which the gastric fistula becomes larger in diameter with time is apt to occur, and consequently, the clearance between the gastric fistula and the feeding tube intubated in the gastric fistula is enlarged. The clearance can be a passage permitting leakage of the enteral nutrition product to the outside of the body due to the inner pressure of the stomach.

To the contrary, the present embodiment, since it allows the enteral nutrition product to be formed as a semi-solid, and since it exhibits the shape retentivity more strongly than a liquid enteral nutrient, provides greater resistance to passing through the same clearance in size. Therefore, the present embodiment would more easily solve the problem of leakage of the enteral nutrition product caused by the inner pressure of the stomach.

Figure 7:
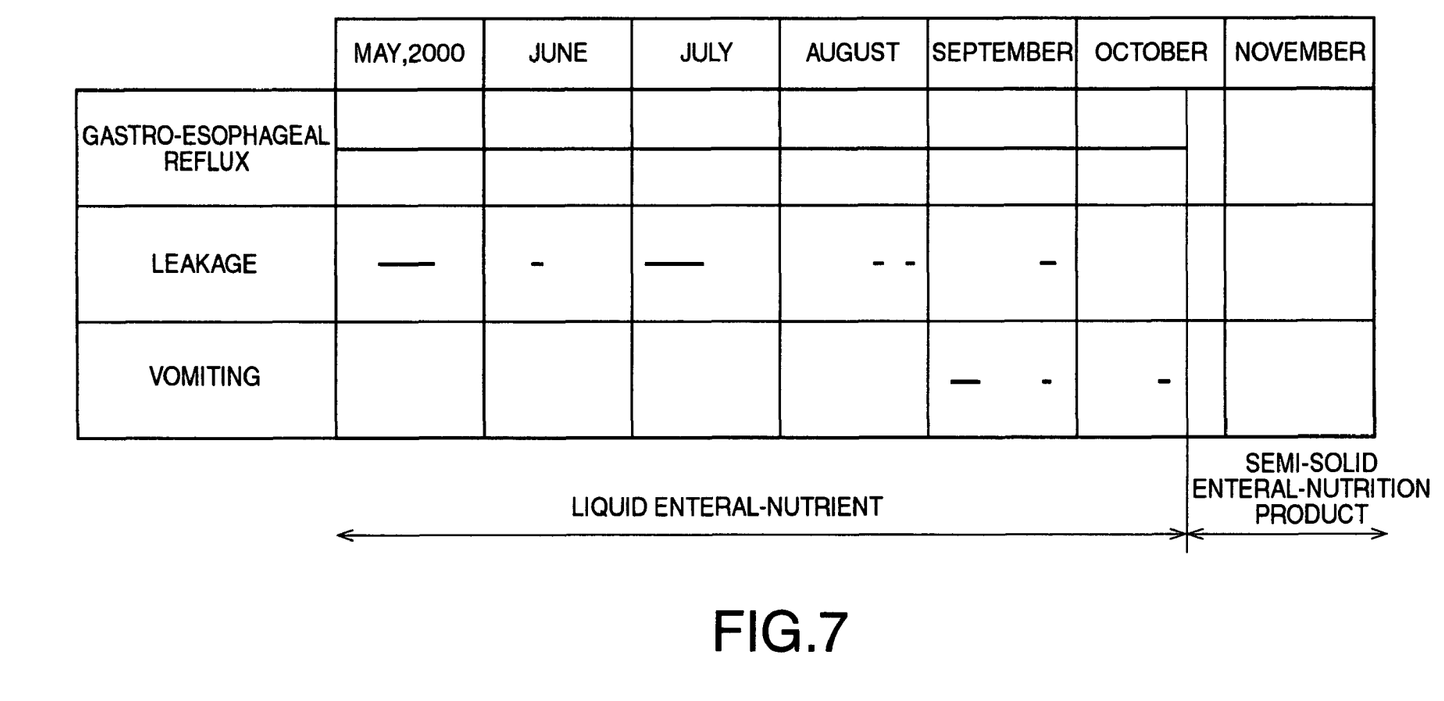
FIG. 7 is a table indicating the results of a clinical trial made for verification of an anti-gastroesophageal-reflux effect, an anti-leakage effect, and an anti-vomiting effect, provided by the enteral nutrition product according to the second embodiment, in comparison with those of a liquid enteral-nutrient.

FIG. 7 shows in time-series the results of the clinical trial conducted for a particular patient (female, 85 years old at that time, in a health care facility for aged people) who underwent endoscopic gastrostomy. The clinical trial was conducted, such that a liquid enteral-nutrient was first administered to the patient, and subsequently, the semi-solid enteral-nutrition product according to the present embodiment was administered the same patient.

As shown in FIG. 7, the clinical trial was conducted, such that during the period from the beginning of May in the year 2000, to the middle of October in the year 2000, a liquid enteral-nutrient was administered to the patient via a gastrostomy. During this period, frequent gastro-esophageal refluxes occurred, and not only the leakage of the liquid enteral-nutrient through the clearance between the gastrostomy and the feeding tube, but also the patient's vomiting was observed.

On the other hand, during the period after the middle of October in the year 2000, the semi-solid enteral-nutrition product was administered to the same patient, instead of the liquid enteral-nutrient. During this period, as shown in FIG. 7, none of gastro-esophageal reflux, leakage, and vomiting were observed.

Therefore, it was verified that the semi-solid enteral-nutrition product in accordance with the present embodiment is more advantageous than a liquid enteral-nutrient, in that the semi-solid enteral-nutrition product enables an easier reduction of both the leakage of the semi-solid enteral-nutrition product and a patient's vomiting, as well.

While several embodiments of the present invention have been described above by reference to the drawings, such description is for illustrative purposes, and the present invention may be carried out in alternative embodiments in which various modifications or improvements may be made of the present invention in light of the teachings of those skilled in the art without departing from the spirit of the present invention.

What is claimed is:

1. An enteral nutrition product for enteral administration, not orally, but directly to a stomach or intestines of a dysphagic patient from an external container connected to an external portion of a feeding tube provided through a through-hole of a stoma formed through a portion of the abdominal and stomach walls of the patient upon the application of pressure to said external container, said enteral nutrition product comprising:
    a semi-solid material having a substantially self-supporting consistency that deforms to flow under an externally applied load without liquefying and that is capable of containing a higher concentration of a nutrient component than a liquid,
    wherein said semi-solid material comprises a mixture of a liquid nutrient solution and a semi-solidifying agent comprising agar that is added to said liquid nutrient solution; and
    wherein said mixture comprises said semi-solidifying agent and said liquid nutrient solution in a predetermined ratio sufficient to ensure that said self-supporting consistency of said semi-solid enteral nutrition product remains substantially unchanged before, during, and after enteral administration of said semi-solid enteral nutrition product into the patient, and said self-supporting consistency of said semi-solid enteral nutrition product is further maintained within the stomach or the intestines of the patient such that said semi-solid enteral nutrition product does not liquefy due to the body temperature of the patient, to thereby prevent the patient from experiencing gastro-esophageal reflux.

2. The enteral nutrition product according to claim 1, wherein said feeding tube has an internal diameter that is larger than approximately 4 mm.

3. A method for preparing the semi-solid enteral nutrition product according to claim 1, comprising the steps of:
    providing a holder comprising said container;
    filling said holder with said mixture of said liquid nutrient solution and said semi-solidifying agent in a liquid state thereof; and
    cooling said mixture within said holder, together with said holder, to thereby prepare said enteral nutritional product.

4. An enteral nutrition product administration device comprising:
    a holder; and
    the enteral nutrition product according to claim 1 provided within said holder;
    wherein said holder comprises said container; and
    wherein said enteral nutrition product is prepared by a method comprising the steps of:
    providing said holder;
    filling said holder with said mixture of said liquid nutrient solution and said semi-solidifying agent; and
    cooling said mixture within said holder, together with said holder, to thereby prepare said enteral nutrition product.

5. The enteral nutrition product according to claim 1, wherein said semi-solidifying agent comprising agar is added in amount of 1 gram to 200 ml of a diluting liquid that is added to said liquid nutrient solution.

6. The enteral nutrition product administration device according to claim 4, containing a required amount of the enteral nutrition product per one batch of administration which is fed into the patient via the feeding tube.

* * * * *